United States Patent [19]

Noiles

[11] Patent Number: 4,602,636
[45] Date of Patent: Jul. 29, 1986

[54] SUTURE WIRE WITH INTEGRAL NEEDLE-LIKE TIP

[75] Inventor: Douglas G. Noiles, New Canaan, Conn.

[73] Assignee: Joint Medical Products Corporation, Stamford, Conn.

[21] Appl. No.: 676,603

[22] Filed: Dec. 3, 1984

Related U.S. Application Data

[63] Continuation of Ser. No. 473,257, Mar. 8, 1983, abandoned.

[51] Int. Cl.$^4$ .............................................. A61B 17/32
[52] U.S. Cl. ................................. 128/335.5; 128/339; 128/92 B; 128/92 E
[58] Field of Search ..................... 128/335.5, 336–337, 128/339, 92 B, 92 E, 335, 334 R; 433/15

[56] References Cited

U.S. PATENT DOCUMENTS

| | | | |
|---|---|---|---|
| 363,478 | 5/1887 | Parsons | 128/339 |
| 2,591,063 | 4/1952 | Goldberg | 128/339 |
| 2,883,096 | 4/1959 | Dawson | 128/339 |
| 3,038,475 | 6/1962 | Orcutt | 128/339 |
| 3,094,123 | 6/1963 | Kurtz | 128/339 |
| 3,233,800 | 2/1966 | Catania | 128/339 |
| 3,311,110 | 3/1967 | Singerman et al. | 128/335.5 |
| 4,535,764 | 8/1985 | Ebert | 128/92 B |

Primary Examiner—Stephen C. Pellegrino
Assistant Examiner—Gene B. Kartchner
Attorney, Agent, or Firm—Maurice M. Klee

[57] ABSTRACT

A monofilament surgical suture wire has a pointed needle-like tip, where the pointed tip is harder and stronger than the balance of the suture wire, is of one homogeneous piece with the wire, and has been made harder and stronger by local cold working.

11 Claims, 5 Drawing Figures

U.S. Patent  Jul. 29, 1986  4,602,636
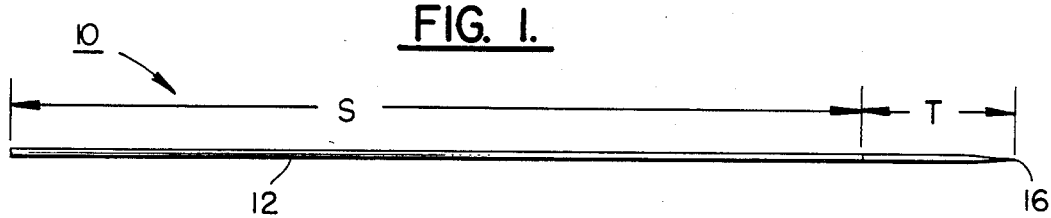
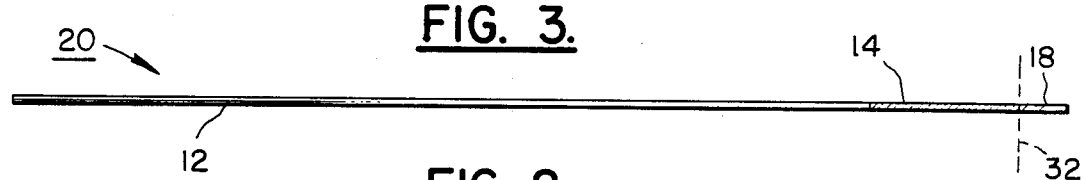
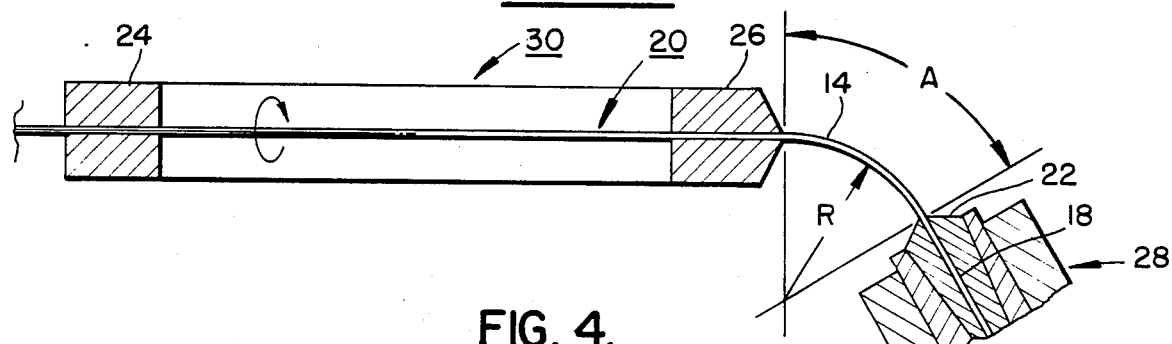
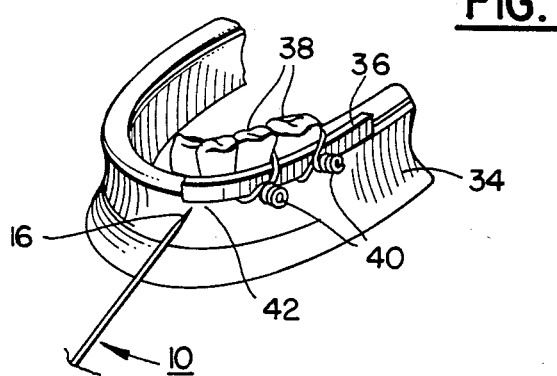
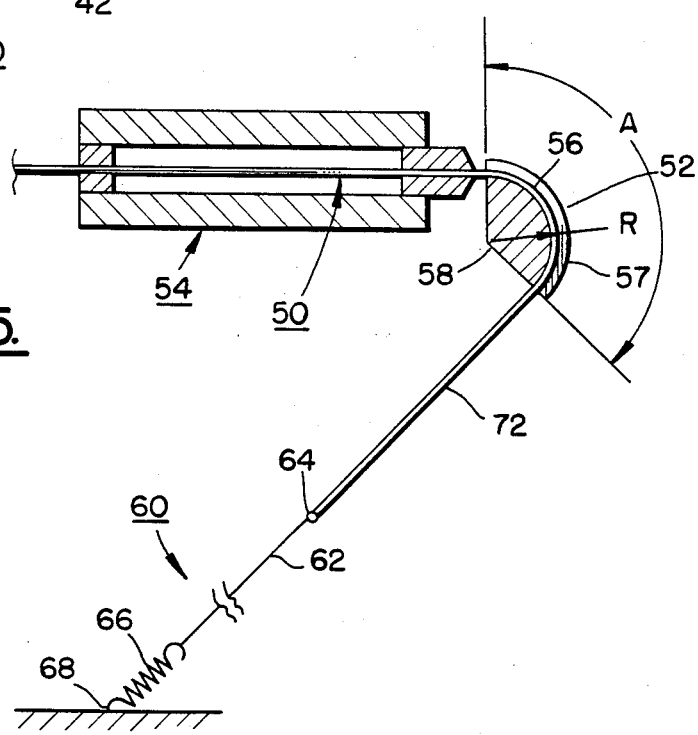

SUTURE WIRE WITH INTEGRAL NEEDLE-LIKE TIP

This is a continuation of (co-pending) application Ser. No. 473,257 filed on Mar. 8, 1983, now abandoned.

BACKGROUND OF THE INVENTION

The present invention relates to a monofilament surgical suture wire which has a pointed needle-like tip where the pointed tip is harder and stronger than the balance of the suture wire, is of one homogenous piece with the wire, and has been made harder and stronger by local cold working. The self needle tipped suture wire of the present invention is particularly useful in the treatment of a fractured jaw.

A fractured jaw is commonly treated by wiring the teeth individually to a support bar shaped to an appropriate arch form. It is customary to use a single relatively short length of monofilament suture wire to fasten each tooth to the arched bar. Each wire is passed around a tooth at or somewhat below the gum line. This is done by pushing the end of the wire through the space between the teeth and often also through the gum tissue. There is presently available no better penetrating tip for such a wire than can be obtained by cutting the wire obliquely with a wire cutter.

Monofilament suture wire is of necessity soft and malleable. It is poorly suited for being pushed between the teeth and through the gum tissue, especially when the penetrating tip is not a sharp point. The present practice of pushing the non-sharp wire tips through the gum tissue causes unnecessary trauma to the tissue which increases the potential for the onset of local infection. In addition, the wire strength is sometimes inadequate to resist buckling under the force required to push the wire between the teeth when high resistance is encountered. Although theoretically the tip of the suture wire could be made pointed, in practice this is difficult to do using conventional manufacturing techniques because the material is soft. In contrast, a hard material is amenable to accepting and holding a sharp edge or point.

Wire sutures with swaged-on needles are available, but are not suitable for wiring fractured jaws because the needle diameter is approximately twice that of the suture wire and there is frequently not enough room to pass such a swaged-on needle between the teeth. In addition, swaged needles are costly and add considerably to the expense of treatment when as many as 24 wires may be used in a single procedure.

Accordingly, a primary object of the present invention is to provide a monofilament suture wire of suitable malleable material with an integral hard and strong needle-like tip.

A further object is to provide a hard strong needle-like tip on a suture wire where the needle-like tip is of no larger diameter than the parent suture wire.

A further object is to provide a needle-like tip for a wire suture at low cost.

A further object is to provide a method for manufacturing a hard and strong needle-like tip from the parent soft malleable suture wire material.

SUMMARY OF THE INVENTION

To achieve these and other objects, the present invention provides a pointed needle-like tip on a length of monofilament surgical suture wire. The pointed tip is harder and stronger than the balance of the suture wire, is of one homogenous piece with the wire, and has been made harder and stronger by local cold working. The invention includes the method by which the tip of the wire is locally cold worked.

In accordance with one aspect of the invention, a surgical suture wire is provided which comprises a length of wire of essentially uniform diameter having first and second portions, the first portion forming one end of the wire and having a greater yield strength and greater hardness than the second portion.

In certain preferred embodiments of the invention the portion of the wire having greater yield strength and greater hardness is created by cold-working that portion of the wire by bending the portion about a curve and rotating the portion about its own axis while bent, said rotation producing strain in the wire, the curvature of the bend being such that for each rotation the strain is greater than that strain which corresponds to the wire's yield strength so that the rotation cold works the bent portion of the wire by producing plastic deformation thereof. In other preferred embodiments, the portion of the wire having greater yield strength and greater hardness is sharpened to a pointed tip. Also, portions having greater yield strength and greater hardness can be placed at both ends of the wire, and such portions can be made curved.

BRIEF DESCRIPTION OF THE DRAWINGS

FIG. 1 shows a suture wire with a hardened and pointed end.

FIG. 2 is a schematic diagram of an equipment arrangement for carrying out the process of the present invention.

FIG. 3 shows the piece of wire created by the process shown in FIG. 2 prior to having a point applied thereto.

FIG. 4 illustrates an application of the surgical wire of the present invention in maxillofacial reconstruction.

FIG. 5 is a schematic diagram of an alternate equipment arrangement for local working of a piece of wire.

DESCRIPTION OF THE PREFERRED EMBODIMENTS

As described above, the present invention relates to a surgical suture wire having an integral harder and stronger needle-like tip. The suture wires are conveniently furnished to the surgeon in lengths of approximately 8 inches. Each suture wire is made with one end hardened and pointed. For other applications sutures may be furnished in other lengths and diameters, and may have both ends hardened and pointed.

Suture wire is commonly made of stainless steel of such alloy as 316LVM. Related stainless steel alloys which can be used in making suture wires are those described in the American Society for Testing and Materials specifications F138-82 and F642-79. In addition, flexible surgical wire can also made of cobalt chromium alloys such as ASTM F 90-82. The present invention is applicable to all of the above alloys, as well as other soft or flexible surgical wire materials which can be work hardened.

From the surgeon's point of view, the performance of the hardened tip of the suture wires of the present invention depends on both the presence of a point on the end of the wire and the yield strength of the tip. As discussed above, hardening the tip allows it to be easily pointed by conventional manufacturing techniques. The higher yield strengths, in combination with the pointed tips, allow the surgeon to push the suture wires between the patient's teeth and through gum tissue, if necessary, without bending. By cold working the normally malleable wire used for making suture wires, it has been found that the wire is both hardened, so that it can receive a pointed tip, and its yield strength is increased, so that it can be pushed between a patient's teeth and through gum material. An increase in yield strength on the order of 25 percent or more has been found adequate to produce these desirable results.

With reference now to the drawings, wherein like reference characters designate like or corresponding parts throughout the several views, there is shown in FIG. 1 a piece of monofilament surgical suture wire 10 according to the present invention. Portion S is that part of wire 10 which is annealed, but not hardened, and is used for surgical fixation and repair by binding, tieing, twisting, etc. Portion S may vary from a few inches to several feet. Portion T is that part of wire 10 which has been work hardened and fashioned to a needle-like point 16. Depending on the application, portion T can have a length of approximately one half to one and one half inches. Although shown straight in FIG. 1, portion T can also be formed in a curve, the same as many surgical needles. The tip can be pointed, sharpened and polished by conventional manufacturing methods.

FIG. 2 shows a spindle 30 which grips wire 20 in a collet 26 and supports wire 20 in guide 24. A second spindle 28 which grips wire 20 at 18 in collet 22 has its center line in the same plane as the center line of spindle 30, i.e., the plane of the paper in FIG. 2. The center line of spindle 28 makes an angle A with the center line of spindle 30 such that part 14 of wire 20 is bent on radius R. Part 14 of wire 20 may be supported in the shape of radius R by an appropriate open or closed bearing.

To perform the work hardening of part 14 of wire 20 the spindles 30 and 28 are rotated in unison. Each revolution causes part 14 of wire 20 to undergo one cycle of stress reversal, as from tension to compression and back to tension. The apparent stress produced in the wire by one revolution is given by the expression:

$$S = \frac{r}{R} \times E$$

where r is the radius of the wire, R is the radius of the bend and E is the Young's modulus of the material of which the wire is composed.

By way of example, a straight 0.020 inch diameter annealed 316LVM stainless steel wire, having a modulus of 28,000,000 lb/in² and bent to a radius of 1 inch, will undergo an apparent stress of:

$$S = \frac{0.01''}{1.00''} \times 28{,}000{,}000 \text{ lb/in}^2 = 280{,}000 \text{ lb/in}^2$$

Annealed 316LVM stainless steel wire typically has a yield stress on the order of 40,000 to 60,000 lb/in². Since the 280,000 lb/in² apparent stress produced by rotation is greater than this yield strength, each rotation of the wire will cause plastic deformation of, and thus cold working of, the bent portion of the wire, i.e. part 14 of wire 20 in FIG. 2. In practice, it has been found that 50 to 150 revolutions using the above conditions will increase the yield strength of wire part 14 by 25% or more.

Other values for radius R can be used so long as the strain created by rotating wire 20 exceeds the strain corresponding to the yield strength of the material. For a given wire material and wire diameter, the value of R and the number of revolutions are adjusted until the desired degree of hardening is achieved.

Angle A, together with radius R, determine the length of wire which will be work hardened. For the above example, if angle A is one radian, part 14 of wire 20 will have a length of one inch.

To remove wire 20 from the apparatus of FIG. 2, collet 22 can be released and spindle 28 retracted in direction B. Wire 20 can then be extracted from spindle 30 and straightened by conventional methods to assume the shape of FIG. 3. Wire part 14 can be left curved if a curved needle-like tip is desired, although in practice it has been found convenient to straighten the wire to facilitate sharpening and then, if desired, curve portion T after sharpening. Before pointing and sharpening, the still soft annealed end part 18 of wire 20 is cut off at 32. The completed suture wire 10, after being pointed and sharpened to form tip 16, is shown in FIG. 1.

FIG. 4 shows schematically the application of wire 10 for repair of a fractured jaw, or maxilla bone 34. A fragment of a bar 36 which has been formed to a shape to match the curvature of the maxilla 34 is shown in FIG. 4. Several teeth are shown at 38. To support the maxilla during healing, the teeth 38 are individually fastened to bar 36 by lengths of suture wire 40 twisted tight. The insertion of a third suture wire 10 between two teeth 38 and below bar 36 at 42 is also shown in FIG. 4. The point of entrance 42 is often through the gum tissue and the space between adjacent teeth may be small. Therefore, sharp point 16 and the increased yield strength obtainable with this invention offers the advantages of making the wire less likely to buckle during insertion and of making a less traumatic wound. Such a cleaner wound normally results in faster healing and affords less opportunity for infection than a ragged puncture. In addition, the sharp point facilitates the procedure for the surgeon.

FIG. 5 shows an alternate equipment arrangement using a single spindle 54. Wire 50 is twice the length of the finished suture. Radius R is appropriate to the wire size and material as described above. Angle A is proportioned so that the bent length 56 of wire 50 is twice the length of the hardened tip T of the finished suture wire 10 of FIG. 1. Bearing block 58 provides an open groove 57 guiding the wire around radius R. Reference numeral 60 indicates a tension device with low torsional resistance. Such a device 60 may consist of a length of braided fishing line fastened to wire 50 at 64 by a small clamp or knot and a tension spring 66 fastened to a fixed point 68.

The function of tension device 60 is to tension wire 50 slightly to keep wire 50 in groove 57 of bearing block 58 and to keep length 72 of wire 50 straight while it rotates on account of rotation of spindle 54. Line member 62 is long enough and otherwise capable of absorbing one hundred or more revolutions of wire part 72 while exerting negligible torque on wire part 72.

After wire 50 has been work hardened and removed from the apparatus of FIG. 5, it is cut at 52, which indicates the mid point of the work hardened length 56, thereby making two lengths, each with a hardened tip. Other processing is as described above.

Although the invention has been illustrated with respect to suture wires used for a fractured jaw reconstruction, it is to be understood that the invention can be used in other medical, surgical and dental procedures where wires having a strong and sharpened end will facilitate execution of the procedure. The term "suture wire" as used in the foregoing specification and the appended claims is to be construed as covering wires suitable for use in such medical, surgical and dental procedures, whether on humans or animals.

What is claimed is:

1. A suture wire comprising a continuous length of a single piece of wire, said continuous length of wire having a uniform chemical composition, an essentially uniform diameter, and a first work hardened portion and a second soft, non-work hardened portion, the first portion forming one end of the length of wire and having a greater yield strength and greater hardness than the second portion.

2. A suture wire according to claim 1 wherein the length of wire includes a third portion, the third portion forming the other end of the wire and having a greater yield strength and greater hardness than the second portion.

3. A suture wire according to claim 1 wherein the first portion is sharpened to a pointed tip.

4. A suture wire according to claim 3 wherein the first portion is curved.

5. A suture wire according to claim 2 wherein the first and third portions are each sharpened to a pointed tip.

6. A suture wire according to claim 5 wherein the first and third portions are curved.

7. A suture wire according to claim 1 wherein the yield strength of the first portion is at least 25 percent greater than the yield strength of the second portion.

8. The suture wire of claim 2 wherein the yield strength of each of the first and third portions is at least 25 percent greater than the yield strength of the second portion.

9. A suture wire according to claim 1 wherein the greater yield strength and greater hardness of the first portion is created by cold-working that portion by bending the portion about a curve and rotating the portion about its own axis while bent, said rotation producing strain in the wire, the curvature of the bend being such that for each rotation the strain is greater than that strain which corresponds to the wire's yield strength so that the rotation cold works the bent portion of the wire by producing plastic deformation thereof.

10. A suture wire according to claim 2 wherein the greater yield strength and greater hardness of each of the first and third portions is created by cold-working that portion by bending the portion about a curve and rotating the portion about its own axis while bent, said rotation producing strain in the wire, the curvature of the bend being such that for each rotation the strain is greater than that strain which corresponds to the wire's yield strength so that the rotation cold works the bent portion of the wire by producing plastic deformation thereof.

11. A method for producing a suture wire from a single piece of wire, said suture wire having a uniform chemical composition, an essentially uniform diameter, and first and second portions, the first portion having a greater yield strength and greater hardness than the second portion, comprising the steps of bending the first portion about a curve and rotating that portion about its own axis while bent, said rotation producing strain in the wire, the curvature of the bend being such that for each rotation the strain is greater than that strain which corresponds to the wire's yield strength so that the rotation cold works the bent portion of the wire by producing plastic deformation thereof.

* * * * *